(12) United States Patent
Zhang

(10) Patent No.: US 11,540,763 B2
(45) Date of Patent: Jan. 3, 2023

(54) CONTROL METHOD AND SYSTEM FOR FILTERING POWER LINE INTERFERENCES

(71) Applicant: MAISONBURG (SHENZHEN) TECHNOLOGY DEVELOPMENT CO., LTD., Shenzhen (CN)

(72) Inventor: Tongsheng Zhang, Shenzhen (CN)

(73) Assignee: MAISONBURG (SHENZHEN) TECHNOLOGY DEVELOPMENT CO., LTD., Shenzhen (CN)

( * ) Notice: Subject to any disclaimer, the term of this patent is extended or adjusted under 35 U.S.C. 154(b) by 259 days.

(21) Appl. No.: 16/645,311

(22) PCT Filed: Sep. 8, 2017

(86) PCT No.: PCT/CN2017/101065
§ 371 (c)(1),
(2) Date: Mar. 6, 2020

(87) PCT Pub. No.: WO2019/047165
PCT Pub. Date: Mar. 14, 2019

(65) Prior Publication Data
US 2020/0297232 A1    Sep. 24, 2020

(51) Int. Cl.
*G01R 29/26* (2006.01)
*A61B 5/00* (2006.01)
(Continued)

(52) U.S. Cl.
CPC .............. *A61B 5/316* (2021.01); *A61B 5/318* (2021.01); *A61B 5/7217* (2013.01); *G01R 13/00* (2013.01); *G01R 29/26* (2013.01)

(58) Field of Classification Search
CPC .. G01R 29/26; A61B 5/00; A61B 5/04; A61B 5/0402
See application file for complete search history.

(56) References Cited

U.S. PATENT DOCUMENTS

| 3,552,386 A | 1/1971 | Horth |
| 6,351,664 B1 | 2/2002 | Brodnick |
| (Continued) | | |

FOREIGN PATENT DOCUMENTS

| CN | 103040459 A | 4/2013 |
| CN | 104783780 | 7/2015 |
| (Continued) | | |

OTHER PUBLICATIONS

"Removal of power-line interference from the ECG: a review of the subtraction procedure"; Levkov et al.; BioMedical Engineering Online; 1BIOMED CENTRAL LTD; vol. 4, No. 1, Aug. 23, 2005.
(Continued)

*Primary Examiner* — Neel D Shah
(74) *Attorney, Agent, or Firm* — Cantor Colburn LLP

(57) ABSTRACT

A control method and system for filtering power line interference is disclosed. The control method includes the following steps. First, ECG signals are pre-segmented and rectified; then the sinusoidal frequency, amplitude, and phase of the rectified segmented signals are extracted. These estimated sinusoidal parameters from each recorded channel are weighted by their individual signal to noise ratios before being averaged to achieve the optimal powerline frequency, amplitude, and phase. Based on these optimal sinusoidal parameters, the individual sinusoidal waveform is reconstructed and then is subtracted from the corresponding ECG segment, in order to obtain the clean ECG signals. This method of filtering the powerline interference through removal from recorded signals enables accurate measurement without any ringing effect that could lead to signal distortion issues. Thus this invention solves the ringing
(Continued)

problem encountered by traditional notch filter techniques when signal amplitude suddenly changes in a measurement.

12 Claims, 4 Drawing Sheets

(51) Int. Cl.
    *A61B 5/316*     (2021.01)
    *G01R 13/00*     (2006.01)
    *A61B 5/318*     (2021.01)

(56) References Cited

U.S. PATENT DOCUMENTS

| | | | |
|---|---|---|---|
| 7,894,885 B2 | 2/2011 | Bartal et al. | |
| 10,602,944 B2* | 3/2020 | Cole | A61B 5/7207 |
| 2014/0288845 A1* | 9/2014 | Mitov | A61B 5/318 702/19 |

FOREIGN PATENT DOCUMENTS

| | | |
|---|---|---|
| CN | 105790729 A | 7/2016 |
| CN | 106125604 | 11/2016 |
| CN | 106667439 | 5/2017 |
| EP | 1987767 A1 | 11/2018 |
| JP | S4922432 B1 | 6/1974 |
| JP | H0630908 A | 2/1994 |
| JP | 2011072725 A | 4/2011 |

OTHER PUBLICATIONS

Supplementary European Search Report for Application No. EP 17 92 4386.
English Machine Translation to Abstract CN104783780.
English Machine Translation to Abstract CN105790729.
English Machine Translation to Abstract CN106125604.
English Machine Translation to Abstract CN106667439.
English Translation of International Search Report for Application No. PCT/CN2017101065.
International Search Report for Application No. PCT/CN2017101065.
Written Opinion for Application No. PCT/CN2017101065.
English Translation of Notice of Reasons for Refusal for Japanese Application No. 2020535280 dated Jul. 26, 2021; 4 Pages.
Machine Translation of JPS4922432B1; 9 Pages.
Notice of Reasons for Refusal for Japanese Application No. 2020535280 dated Jul. 26, 2021; 4 Pages.

\* cited by examiner

CONTROL METHOD AND SYSTEM FOR FILTERING POWER LINE INTERFERENCES

CROSS REFERENCE TO RELATED APPLICATIONS

This application is a National Stage of PCT Application No. PCT/CN2017/101065 filed on Sep. 8, 2017, the contents of which are incorporated herein by reference thereto.

TECHNICAL FIELD

The invention belongs to the technical field of signal filtering; in particular, it relates to a control method and a control system for filtering out power line interference from electrocardiogram (ECG) signals.

PRIOR ART

Electrocardiography (ECG) is widely used as a vital physiological index in clinical applications. However, measurements of human ECGs in hospitals are often contaminated by power line interferences. The complex electrical environment in which these measurements are made makes these kinds of interferences ubiquitous. Such power line interferences can be characterized as sinusoidal waveforms with 50/60 Hz fundamental frequencies and higher harmonics, wherein the 50 Hz fundamental frequency dominates in Asia and Europe while 60 Hz dominates in northern American power supply systems. The frequency band of the conventional ECG ranges from 0.05 up to 100 Hz, the high-frequency QRS analysis ranges from 80 to 300 Hz, and while the frequency band of the Ventricular Late Potentials (VLPs) is even higher, up to 500 Hz. These ranges correspond to the $2^{nd}$, $6^{th}$, and $10^{th}$ harmonics of the 50 Hz power line interference, respectively. Additionally, the power line frequencies themselves are not absolutely constant, but can change by up to ±2 Hz over time. Consequently, power line interferences are important noise sources that often hinder the analysis of ECG signals.

Thus, in practice, ECG detection machines are often equipped with notch filters or other similar filters to allow operators to eliminate power line interference. However, if there is a non-stationary electromagnetic impact in the measurement environment, the embedded linear filter in ECG machines cannot reliably remove power line inferences. For instance, a notch filter by means of a narrow band stop filter often causes ringing right after a large pulse, which presents an additional interference to the signal. This ringing due to a sudden amplitude change by a conventional notch filter is schematically illustrated in FIG. 1, where the sub-figure at left is the original one-beat of a typical ECG, while the right sub-figure shows this ECG signal after passing through a very narrow notch filter. Here the larger QRS wavelet plays the role of a sudden pulse, and after processing by the notch filter, a ringing is observed at the end of the QRS complex (see the right sub-figure in FIG. 1 immediately following QRS). This ringing complicates the observation of the real information in the signal.

As shown in FIG. 1, the narrower the notch filter stop frequency band employed, the more severe the ringing effect on the signal. However, the wider the stop frequency band used, the greater the number of signals prone to loss besides power line frequency interferences. These limitations negatively affect many otherwise useful applications; for example, the VLPs reflecting myocardial infarction happen to fall into the ST segment at the end of a QRS complex and their amplitude is only 3-25 micro volts (uV), while their frequency ranges from 40 Hz through 500 Hz. Any ringing incurred by a notch filter after a QRS complex would mask these VLPs. Therefore, the use of notch filter techniques implemented by either hardware or software is not allowed by major heart associations worldwide in their published measurement standards. Due to this ban, VLP measurements in clinical applications suffer from much interference.

In order to solve the ringing problems after a sudden signal or interference amplitude change caused by a conventional notch filter, many alternative technologies have been adopted to improve the notch filter performance. Among them, one useful class of techniques is called adaptive filtering. In general, these techniques remove power line interference and other types of noise by developing a time-varying matched filter, with an additional channel to provide reference data. Adaptive filtering techniques may solve the ringing response following a sudden amplitude change such as with the QRS complex, but they still suffer from finite response times and are not always satisfactory in VLP detection. Such problems are inherent to the technology and difficult to correct.

Another technique for filtering out power line interference is to have one or more additional channels provide reference interference. Due to the orthogonality of the interesting signal to the interference, the least square approach can be utilized to project the interference into the measured data space in order to remove the projections of the interference in the data. Similarly, the methods of Principal Component Analysis (PCA) and Independent Component Analysis (ICA), are also often used to separate the power line interference from the signals. In the former method the power line interference is counted as the principal component, while in the latter method, the power line interference is taken as an independent source.

Yet another technique is to extract the power line interference from the linear ECG signal segment between the end of the previous QRS complex and the beginning of the next QRS complex. Then this power line inference is extrapolated to the non-linear QRS area and is then subtracted from the raw ECG in order to achieve a clean signal. Although this method is very helpful in solving the ringing problem caused by conventional notch filters, there are two potential issues. First, there is a bandwidth dilemma when applying the band pass filter to extract the power line interference in the linear region. Setting the bandwidth wider would cause the loss of signals in spite of favoring the power line frequency change, whereas setting the bandwidth too narrow could lead to missing the power line interference entirely since the power line frequency may change over the preset range. Second, if removing higher order harmonics is required, a comb filter has to be implemented, which further complicates the system and leads to more signal loss in the vicinities of the higher order harmonic frequencies.

In summary, the current filtering technologies suffer from various issues related to either loss or distortion of signals as mentioned above when removing power line interferences. This kind of distortion is especially critical in high frequency ECG analysis, for example, the high frequency QRS analysis and VLPs detection.

Technique Problem to Solve in this Invention

This invention provides a solution and a system to eliminate the power line interference in a signal, aimed at solving the potential ringing problem caused by a conventional notch filter which can distort or even mask a signal. More generally, the disclosed approach in this invention solves the potential issues incurred when a conventional notch filter is applied, to offer a novel narrow band stop filtering technique. It is highly applicable to high frequency QRS analysis and Ventricular Late Potentials detection.

Technique Problem Solving Approach

Firstly, the invention discloses a control method to filter out power line interference. The said method contains:

Rectifying a preset segment of signal that is for filtering power line interference;

Estimating the sinusoidal parameters of the rectified segment, i.e., frequency, amplitude and phase, corresponding to the power line interference;

Based on the above estimated frequency (divided by 2), extracting the sinusoidal amplitude and phase from the said segment of signal;

Reconstructing the sinusoidal waveform based on the said frequency, said amplitude, and said phase;

Subtracting the said reconstructed sinusoidal waveform from said segment of signal, to output a clean signal.

Secondly, the invention discloses a control system to filter out power line interference. Said system contains;

Rectifier Module, to rectify the preset segment of signal;

Extracting Parameter Module, to extract the said sinusoidal parameters from said rectified segment of signal. The said sinusoidal parameters include frequency, amplitude and phase of the power line interference;

Reconstruction Sinusoidal Waveform Module, to reconstruct the said sinusoidal waveform based on the said parameters;

Thirdly, the invention discloses an ECG measurement system including data storage, processor, and a program embedded in said processor to carry out processing said data saved in said storage. The said program runs in the said processor to implement the said control steps.

Fourthly, the invention discloses a computer readable memory media. The said media saves a computer program, and the said program runs in the said processor to implement the said steps.

Benefit of the Invention

This invention provides a power line frequency interference control method and system. The control system contains the following procedure: firstly taking a segment of ECG signal for each channel and get them rectified; then extracting the sinusoidal parameters for each channel, i.e., frequency, amplitude, and phase, for the power line interference. Then based on the said parameters and by utilizing the signal to noise ratio of each channel as a weighing factor, it optimizes the power line frequency and phase of all recording channels in the system, as well as the amplitude of each individual channel, to construct the power line interference. For each channel the power line interference sinusoidal waveform is subsequently reconstructed and then subtracted from the said segment of signal, in order to obtain a clean signal. Thus filtering out of the power line interference is accomplished without the ringing effect on the signal after a huge transient interference, which allows the measurement to be made with high fidelity and accuracy. Consequently, the invention solves the problems with the conventional notch filtering technology.

DETAILED DESCRIPTION OF IMPLEMENTATION

In order to elucidate the technical approach of and the problems solved by the invention, the present invention will be further described in detail below with reference to the accompanying drawings and embodiments. It is understood that the specific embodiments described herein are merely illustrative of the invention and are not intended to limit the invention.

The solution provides a control method and a control system for filtering the power frequency interference signal, wherein the control method comprises the following: First, each channel of the multi-channel ECG signal is segmented around the QRS wave, and the segmented signal is rectified. This nonlinear processing doubles the frequency of the original power frequency interference signal, for example, from 50 Hz to 100 Hz, thereby improving the accuracy of detecting the interference frequency. The frequency, amplitude, and phase of the power frequency interference signal in the ECG recordings of each channel of the rectified preset section are then obtained. The optimal frequency and phase values are then comprehensively determined. The estimated power frequency interference signal sine wave is reconstructed according to the determined frequency, amplitude and phase. Finally, the sine wave signal constructed by each channel is subtracted from the preset segment (signal) of the raw ECG signal, outputting the clean waveform signal. Thereby, the effect of filtering out the power frequency interference signal without generating a ringing effect is achieved, so that the measurement is more accurate. In the explanation process of the present invention, the term signal not only represents a signal in the usual sense, but also represents the power frequency interference to be extracted.

In order to explain the technical solutions described in the present invention, the following description delineates the specific embodiments.

Figure 1:
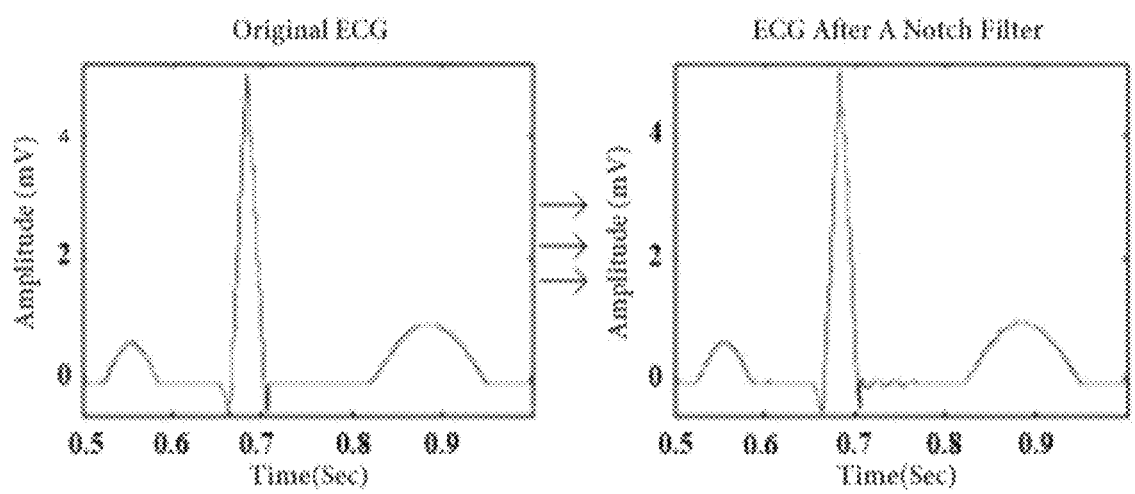
FIG. 1 illustrates the comparison of a segment of ECG without (left) and with (right) filtering by a conventional power line notch filter schematically.
Figure 2:
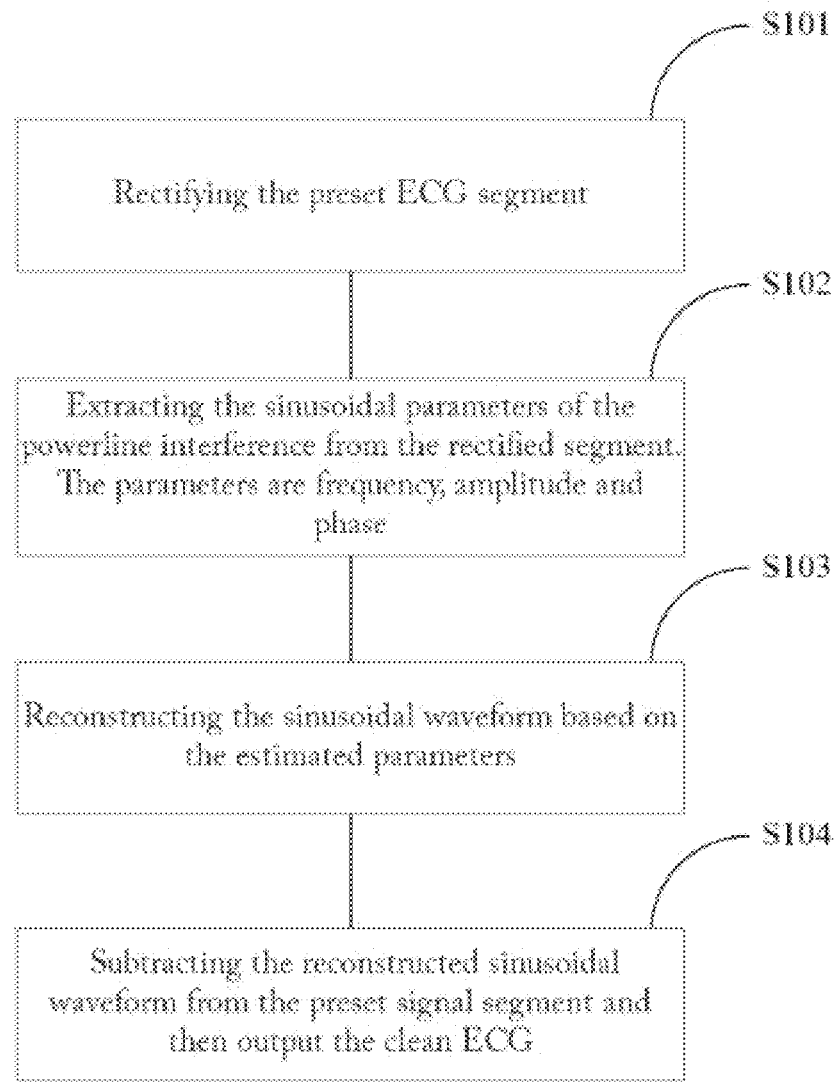
FIG. 2 is a flow chart of an embodiment of the present invention to filter the power line interference.

FIG. 2 is a flow chart showing a step for a control method to filter out a power frequency interference signal according to an embodiment of the present invention. For convenience of description, only parts related to the embodiment of the present invention are shown, which are as follows:

The above-mentioned control method for filtering out the power frequency interference signal comprises the following steps:

S101. Rectify the raw ECG signal of the preset section.

The raw ECG signal is the ECG signal of the human body detected by the ECG detection device. Since the raw ECG signal is rectified, the frequency (the fundamental wave and all harmonics) of the original power frequency interference signal is doubled; for example, for a 50 Hz fundamental frequency power frequency interference signal, the frequency becomes 100 Hz after rectification. Segmented signals of the same length of time then contain twice as many periodic signals (including power frequency interference signals). Previous studies have shown that the higher the frequency, the more cycles are included in the same time period, which increases the accuracy of the estimated frequency.

S102. Acquire the parameters of a power frequency interference signal in the ECG signal of the rectified preset segment, where the parameters include frequency, amplitude, and phase.

The frequency, amplitude and phase of the power frequency interference signal in the ECG signal of the rectified preset segment are obtained based on the RAW-STEM method. Of course, the frequency is divided by 2 to obtain the estimated power frequency interference of the current channel in the current time period. That is, the estimated frequency value of the power frequency interference signal of the current channel in the current time period is obtained. At the same time, the standard deviation SD of the preset segment data is calculated. The ratio of the amplitude of the preset segment data extraction to the standard deviation is defined as the signal-to-noise ratio of the channel, from which the accuracy of the estimated frequency, amplitude, and phase can be determined. The higher the ratio, the more accurate the estimated parameters.

Since the raw ECG signal has multiple channels, all the channels form a database composed of the power frequency interference signals of all the preset segment data at all times, and the database is an estimated value of the above three parameters of frequency, amplitude and phase, wherein the exact reliability of the amplitude estimate is measured by the ratio of the amplitude estimate to the standard deviation of the channel during that time period.

Using the ratio of the extracted amplitude to the standard deviation as the weighting factor, the estimated frequencies in the selected best SNR channels are weighted and averaged, as described in equation (1), to further optimize the accuracy of the parameter estimation:

$$f_0 = \frac{1}{\sum_{n=1}^{L} \frac{a_n}{SD_n}} \cdot \sum_{n=1}^{L} \frac{a_n}{SD_n} f_n \quad (1)$$

Where L is the number of channels with the highest signal-to-noise ratio selected in the raw ECG signal, $a_n$ is the amplitude of the power-frequency interference signal of the nth channel estimated by the RAW-STEM method, $SD_n$ is the standard deviation of the nth channel at the current time, $f_n$ is the frequency estimate of the power frequency interference signal of the current channel at the current time, and $f_o$ is the optimized estimated frequency of the power frequency interference signal of all channels of the entire measurement system. Where $L \in 3$ (ventricular late potential measurement) or $L \in 12$ (conventional ECG measurement). For clinical routine electric encephalograph (EEG), L=32 signals, and for modern magnetoencephalography (MEG) equipment, the number of channels may be as high as 306. Of course, if the number of channels is small, for example for traditional ventricular late potential measurements that only require three channels, then L selects all channels.

The above formula indicates an assumption that the higher the signal-to-noise ratio, the more accurate the estimated frequency, and therefore the higher the contribution to the estimate of the optimal frequency. The weight is used to find the optimal frequency. For the background noise and physiological information, the estimation of the parameters of the power frequency interference signal always fluctuates around the correct value. Therefore, such a weighted average further optimizes the accuracy of the parameter estimation.

The amplitude of each channel at each moment is a relatively complex physical quantity. Assuming that the spatial position of the interference source is unchanged relative to the multi-channel measurement system, then the ratio of the fundamental wave to any harmonic amplitude of the power frequency interference signal observed by each channel would remains unchanged. Therefore, select the time when the signal-to-noise ratio of all channels is the highest, and obtain the amplitude values of each channel at these moments, and then use the weighting method of formula (1) where the fn is replaced by amplitude an, in order to calculate the ratios of all amplitudes in all channels. These ratio stays constant for a given system and therefore, at any time, using this proportional relationship and the amplitude value provided by one or several channels with the highest signal to noise ratios at that time, the amplitude of the remaining lower signal to noise ratio channels at that time can be found. According to the RAW-STEM algorithm, the QRS wave is replaced by the estimated and reconstructed sinusoidal wave based on the above formula (1) clipped corresponding to the time window. Then Amplitude-frequency spectral analysis (ie, FFT) is performed on this updated segment of signal. Then, the frequency value f0 is found in the amplitude-frequency spectrum. In general, f0 does not necessarily coincide exactly with the frequency point of the discrete amplitude-frequency spectrum. Let f0 be the two points before and after the adjacent amplitudes a and b, where a is greater than b. Then the frequency difference $\Delta bin$ of the larger of f0 and a, b can be obtained. Thus, the optimal amplitude estimation of the power frequency interference signal of the preset section is determined by the formula (2):

$$A = 2a \frac{\pi \cdot \Delta bin}{\sin(\pi \cdot \Delta bin)} (1 - \Delta bin^2) \quad (2)$$

For the phase estimation values of the foregoing channels, there are two possibilities. One is that all channels tend to one value, and the other is that the phases of all channels tend to two values that are 180° out of phase (for example, some differential input amplification channels and biomagnetic gradient signal measurements). In either case, employing the similar optimization equation (1) where $f_n$ is replaced by the phase, then an accurate phase is estimated. The phase optimization procedure can be re-written as in the following formula (3):

$$\phi_0 = \frac{1}{\sum_{n=1}^{L} \frac{a_n}{SD_n}} \cdot \sum_{n=1}^{L} \frac{A_n}{SD_n} \phi_n \quad (3)$$

The initial phase $\phi n$ of the ECG signal of the rectified preset segment is determined by the RAW-STEM algorithm, and the signal-to-noise ratio is determined by the latest estimated amplitude An and the variance $SD_n$ after the QRS wave is replaced by the reconstructed sinusoidal waveform in the segment signal.

The estimation of amplitude, frequency and phase are repeatedly carried out according to the above-mentioned formulas for frequency, amplitude, and phase. This iterative operation ends if the maximum change in the amplitude values of all channels of the (i+1)th estimate is smaller than the ith estimate by some pre-selected value, such as 0.1%.

The result is maximally close to the optimal data, which ensures the overall filtering scheme has a high precision effect.

S103. Construct an estimated power frequency interference sinusoidal waveform based on the above estimated frequency, amplitude, and phase.

Combining the frequency, amplitude and phase obtained and estimated above, reconstruct the power frequency interference sinusoidal wave to compare with the waveform of the raw ECG signal.

S104. Subtract the reconstructed sine wave signal from the preset segment of the raw ECG signal to output a clean waveform signal.

By subtracting the sine wave signal from the preset segment (signal) of the raw ECG signal, the waveform signal after filtering the power frequency interference signal can be obtained, thereby realizing the effect of filtering out the power frequency interference signal from the ECG signal.

The above description is only for one of the preset sections of the raw ECG signal, and the principle can be extended to all sections of the raw ECG signal.

In an embodiment of the invention, before the rectifying the ECG signal of the preset segment, the method further includes the following steps:

S100. The ECG signals of each channel are segmented around each QRS wave. Each segment is defined as starting from the end of the previous QRS wave and ending at the beginning of the next QRS wave. Thus, except for the signal before the first QRS wave and after the last QRS wave, the linear zone between all QRS waves is reused.

QRS wave refers to the largest amplitude group in normal ECG measurements, reflecting the whole process of ventricular depolarization. Normal ventricular depolarization begins in the middle of the interventricular septum and depolarizes from the left side to the right, so the QRS complex first presents a small downward q wave. The shape of the detected QRS complex wavelets is consistent between individuals. The normal adult QRS group time is 0.06-0.10 s, while for infants and young children the group time is 0.04-0.08 s.

Therefore, the principle of the above control method for filtering out the power frequency interference signal is specifically: the first step is to replace the nonlinear QRS wave with the mean value of the segment signal, find the three parameters of the sine wave described, and reconstruct the sine wave obtained in this step; in the second step, the sine wave reconstructed in the first step is cut corresponding to the portion of the QRS wave, the QRS wave of the segment signal is replaced, the three parameters of the power frequency interference contained in the signal that replaces the QRS wave is estimated, and the power frequency interference sine wave signal according to the new parameters just obtained is reconstructed and defined as S2; in the third step, the sine wave reconstructed in the previous step is cut corresponding to the interference signal in the QRS band to replace the signal being analyzed, the three basic parameters of the power frequency interference sine wave included in the segment signal are analyzed and extracted, and the power frequency interference sine wave is reconstructed with these three basic parameters and defined as S3; in the fourth step, the percentage of the variation of the interference sine wave estimated by the above two steps is calculated, that is, RMS(S3−S2)/RMS(S2)×100%, and compared to a certain preset value such as 0.1%. If it is smaller than or equal to the preset value, it is convergent, and the analysis processing of the segment signal is ended; if it is greater than the preset value, the foregoing steps are repeated until the convergence condition is satisfied. The same iterative estimation to obtain the power frequency interference sine wave parameters for the QRS segment of each ECG channel is done for all ECG channels.

As an embodiment of the present invention for analyzing and extracting power frequency electrical interference, for the convenience of description, the power frequency electrical interference is regarded as a kind of signal, and other components such as white noise and electrocardiographic signals are used as noise when analyzing power frequency interference. Three parameters of the electrical interference sine wave (power frequency interference signal) are extracted: frequency, amplitude, and phase, to reconstruct the sine wave interference. The frequency varies from the fundamental (50 hz in China) to all harmonic changes in the upper frequency range of the measurement range.

As an embodiment of the present invention, the above control method can be used as post-processing of the raw ECG signal, or can be solidified into a digital signal processing chip and directly applied to the measuring instrument for real-time analysis and processing; of course, it can be applied to all fields of biomedical multi-channel measurements such as EEG, magnetoencephalography (MEG), etc., and can also be applied to all measurement control fields involving power frequency electrical interference. And the above control method can be applied to the power frequency filtering replacement technology in the electrocardiographic monitoring instrument involved in the common electrocardiogram, or applied to the ventricular late potential examination, or applied to the high frequency QRS wave analysis technology.

Figure 3:
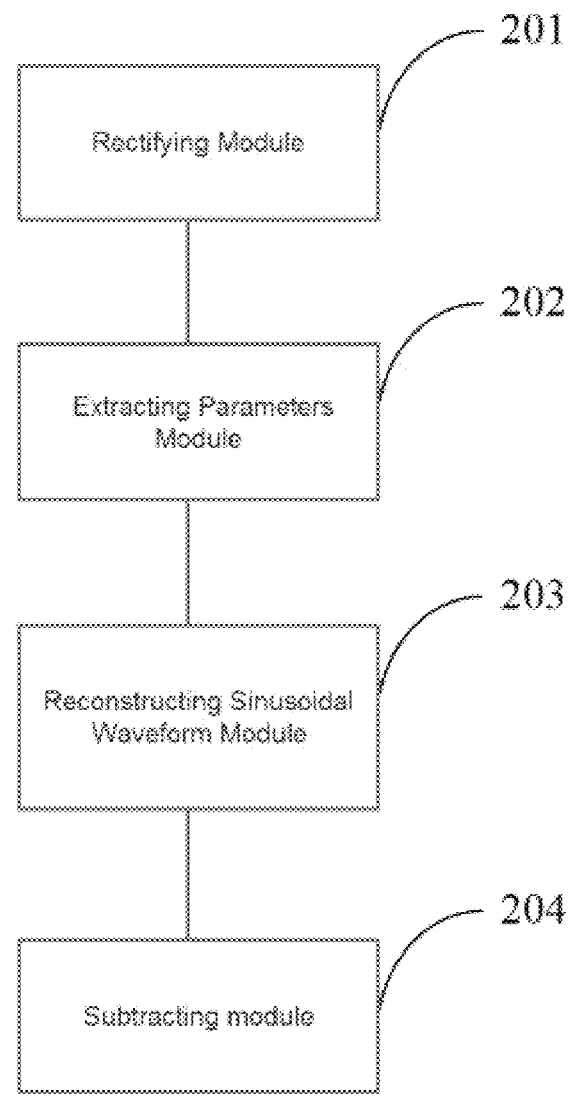
FIG. 3 is a schematic modular structural diagram of an embodiment of the current invention.

FIG. 3 is a block diagram showing a module structure of a control system for filtering power frequency interference signals according to an embodiment of the present invention. For convenience of description, only parts related to the embodiments of the present invention are shown, which are described in detail as follows:

The above control system for filtering power frequency interference signals comprises: The rectifier module 201 is configured to rectify the raw ECG signal of the preset segment.

The raw ECG signal is the ECG signal of the human body detected by the ECG detection device. Since the raw ECG signal is rectified, the frequency (the fundamental wave and all harmonics) of the original power frequency interference signal is doubled; for example, for a 50 Hz fundamental frequency power frequency interference signal, the frequency becomes 100 Hz after rectification. Segmented signals of the same length of time then contain twice as many periodic signals (including power frequency interference signals). Previous studies have shown that the higher the frequency, the more cycles are included in the same time period, which increases the accuracy of the estimated frequency.

The parameter obtaining module 202 is configured to acquire parameters of the power frequency interference signal in the ECG signal of the rectified preset segment, where the parameters include frequency, amplitude, and phase.

The frequency, amplitude and phase of the power frequency interference signal in the ECG signal of the rectified preset segment are obtained based on the RAW-STEM method. Of course, the frequency is divided by 2 to obtain the estimated power frequency interference of the current channel in the current time period. That is, the estimated frequency value of the power frequency interference signal of the current channel in the current time period is obtained. At the same time, the standard deviation SD of the preset segment data is calculated. The ratio of the amplitude of the preset segment data extraction to the standard deviation is defined as the signal-to-noise ratio of the channel, from which the accuracy of the estimated frequency, amplitude, and phase can be determined. The higher the ratio, the more accurate the estimated parameters.

Since the raw ECG signal has multiple channels, all the channels form a database composed of the power frequency interference signals of all the preset segment data at all times, and the database is an estimated value of the above three parameters of frequency, amplitude and phase, wherein the exact reliability of the amplitude estimate is measured by the ratio of the amplitude estimate to the standard deviation of the channel during that time period.

Using the ratio of the extracted amplitude to the standard deviation as the weighting factor, the estimated frequencies in the best SNR are weighted and averaged, as described in equation (1), to further optimize the accuracy of the parameter estimation:

$$f_0 = \frac{1}{\sum_{n=1}^{L} \frac{a_n}{SD_n}} \cdot \sum_{n=1}^{L} \frac{a_n}{SD_n} f_n \qquad (1)$$

Where L is the number of channels with the highest signal-to-noise ratio selected in the raw ECG signal, an is the amplitude of the power-frequency interference signal of the nth channel estimated by the RAW-STEM method, $SD_n$ is the standard deviation of the nth channel at the current time, $f_n$ is the frequency estimate of the power frequency interference signal of the current channel at the current time, and $f_o$ is the current estimated frequency of the power frequency interference signal of all channels of the entire measurement system. $L \in 3$ (ventricular late potential measurement) or $L \in 12$ (conventional ECG measurement). For clinical routine ECG, L=3 signals, and for modern magnetoencephalography (MEG) equipment, the number of channels may be as high as 306. Of course, if the number of channels is small, for example for traditional ventricular late potential measurements that only require three channels, then L selects all channels.

The above formula presupposes the assumption that the higher the signal-to-noise ratio, the more reliable the estimated frequency, and therefore the higher the contribution to the estimate of the optimal frequency. The weight is used to find the optimal frequency. For the background noise and physiological information, the estimation of the parameters of the power frequency interference signal always fluctuates around the correct value. Therefore, such a weighted average further optimizes the accuracy of the parameter estimation.

The amplitude of each channel at each moment is a relatively complex physical quantity. Assuming that the spatial position of the interference source is unchanged relative to the multi-channel measurement system, then the ratio of the fundamental wave to any subharmonic amplitude of the power frequency interference signal observed by each channel remains unchanged. Therefore, select the time when the signal-to-noise ratio of all channels is the highest, and obtain the amplitude values of each channel at these moments, and use the weighting method of formula (1). $f_n$ is replaced by the corresponding amplitude estimation value of each channel, and the ratio of the amplitude of each channel is calculated. Therefore, at any time, using the proportional relationship and the amplitude value provided by one or several of the highest signal to noise ratios at that time, the amplitude of the remaining lower signal to noise ratio channels at that time can be found. According to the RAW-STEM algorithm, the QRS wave is replaced by the frequency corresponding to the time window as in the above formula (1), and the amplitude and phase are determined by the RAW-STEM method acting on the preset segment signal. Amplitude-frequency spectral analysis (ie, FFT) is performed on the reconstructed signal. Then, the frequency value f0 determined by the corresponding formula (1) is found in the amplitude-frequency spectrum. In general, f0 does not necessarily coincide exactly with the frequency point of the discrete amplitude-frequency spectrum. Let $f_o$ be the two points before and after the adjacent amplitudes a and b, where a is greater than b. Then the frequency difference $\Delta bin$ of the larger of $f_0$ and a, b can be obtained. Thus, the optimal amplitude estimation of the power frequency interference signal of the preset section is determined by the formula (2):

$$A = 2a \frac{\pi \cdot \Delta bin}{\sin(\pi \cdot \Delta bin)} (1 - \Delta bin^2) \qquad (2)$$

For the phase estimation values of the foregoing channels, there are two possibilities. One is that all channels tend to one value, and the other is that the phases of all channels tend to two values that are 180° out of phase (for example, some differential input amplification channels and biomagnetic signal measurements). In either case, the $f_n$ in equation (1) is replaced by the phase estimate of each channel that tends to be consistent, and an accurate phase $\emptyset_0$ is estimated, which uses the following formula (3):

$$\emptyset_0 = \frac{1}{\sum_{n=1}^{L} \frac{a_n}{SD_n}} \cdot \sum_{n=1}^{L} \frac{A_n}{SD_n} \emptyset_n \qquad (3)$$

The initial phase $\emptyset_n$ of the ECG signal of the rectified preset segment is determined by the RAW-STEM algorithm, and the signal-to-noise ratio is determined by the latest estimated amplitude $A_n$ and the variance $SD_n$ after the QRS wave is estimated by the waveform in the segment signal.

Repeatedly estimate according to the above-mentioned formulas for frequency, amplitude, and phase. This iterative operation of this step ends if the maximum change in the amplitude values of all channels of the (i+1)th estimate is smaller than the ith estimate by some pre-selected value, such as 0.1%. The result is that the maximum is close to the optimal data, and the overall filtering scheme has a high precision effect.

The sine wave construction module 203 is configured to construct a sine wave according to the frequency, amplitude and phase.

Combining the frequency, amplitude and phase obtained and estimated above, a sine wave model is established to compare with the waveform of the raw ECG signal.

The filtering module 204 is configured to subtract the reconstructed sine wave signal from the preset segment of the raw ECG signal to output a clean waveform signal.

By subtracting the sine wave signal from the preset segment (signal) of the raw ECG signal, the waveform signal after filtering the power frequency interference signal can be obtained, thereby realizing the effect of filtering out the power frequency interference signal from the ECG signal.

The above description is only for one of the preset sections of the raw ECG signal, and the principle can be extended to all sections of the raw ECG signal.

As an embodiment of the present invention, the foregoing control system further includes:

The preset section dividing module is configured to select a plurality of preset sections in the raw ECG signal, and each preset section uses two adjacent QRS waves as reference objects, starting from the end of the first QRS wave and ending at the beginning of the second QRS wave.

QRS wave refers to the largest amplitude group in normal ECG measurements, reflecting the whole process of ventricular depolarization. Normal ventricular depolarization begins in the middle of the interventricular septum and depolarizes from the left side to the right, so the QRS complex first presents a small downward q wave. The shape of the detected QRS complex wavelets is consistent between individuals. The normal adult QRS group time is 0.06-0.10 s, while for infants and young children the group time is 0.04-0.08 s.

As an embodiment of the present invention for analyzing and extracting power frequency electrical interference, for the convenience of description, the power frequency electrical interference is regarded as a kind of signal, and other components such as white noise and electrocardiographic signals are used as noise when analyzing power frequency interference. Three parameters of the electrical interference sine wave (power frequency interference signal) are extracted: frequency, amplitude, and phase, to reconstruct the sine wave interference. The frequency varies from the fundamental (50 hz in China) to all harmonic changes in the upper frequency range of the measurement range.

Figure 4:
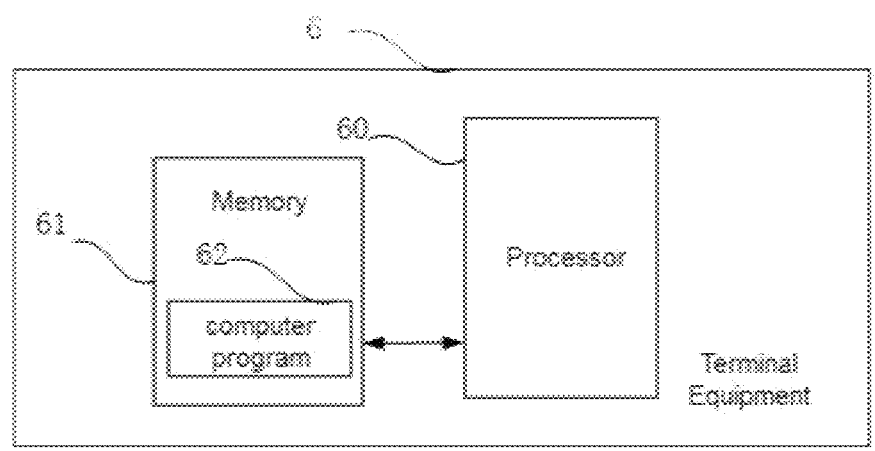
FIG. 4 is a schematic diagram of an ECG signal measuring apparatus according to this embodiment of the present invention.

FIG. 4 is a schematic diagram of an electrocardiographic signal measuring apparatus according to an embodiment of the present invention. As shown in FIG. 4, the electrocardiographic signal measuring apparatus 6 of this embodiment includes a processor 60, a memory 61, and a computer program 62, such as an electrocardiographic signal processing program, stored in the memory 61 and operable on the processor 60. When the processor 60 executes the computer program 62, the steps in the above various control method embodiments are implemented, such as steps S101 to S104 shown in FIG. 2. Alternatively, when the processor 60 executes the computer program 62, the functions of the modules/units in the above various device embodiments are implemented, such as the functions of the modules 201 to 204 shown in FIG. 3.

Illustratively, the computer program 62 can be partitioned into one or more modules/units that are stored in the memory 61 and executed by the processor 60 as an embodiment of this invention. The one or more modules/units may be a series of computer program instructions that are capable of performing a particular function, the instruction segments being used to describe the execution of the computer program 62 in the ECG signal measuring device 6. For example, the computer program 62 can be divided into a synchronization module, a summary module, an acquisition module, and a return module (modules in a virtual device), and the specific functions of each module are as follows:

The ECG signal measuring device 6 may be a computing device such as a desktop computer, a notebook, a palmtop computer, or a cloud server. The ECG signal measuring device may include, but is not limited to, a processor 60 and a memory 61. It will be understood by those skilled in the art that FIG. 4 is merely an example of the electrocardiographic signal measuring device 6, and does not constitute a limitation on the electrocardiographic signal measuring device 6, and may include more or fewer components than those illustrated, and may combine components, and may use different components. For example, the ECG signal measuring device may further include and input/output device, a network access device, a bus, and the like.

The processor 60 may be a central processing unit (CPU), a general-purpose processor, a digital signal processor (DSP), an application specific integrated circuit (ASIC), a field-programmable gate array (FPGA) or other programmable logic device, a discrete gate or transistor logic device, discrete hardware components, etc. The general purpose processor may be a microprocessor or any conventional processor or the like.

The memory 61 may be an internal storage unit of the electrocardiographic signal measuring device 6, such as a hard disk or a memory of the electrocardiographic signal measuring device 6. The memory 61 may also be an external storage device of the electrocardiographic signal measuring device 6, such as a plug-in hard disk equipped with the ECG signal measuring device 6, a smart memory card (SMC), or a secure digital device (Secure Digital, SD) card, flash card, etc. Further, the memory 61 may also include both an internal storage unit of the ECG signal measuring device 6 and an external storage device. The memory 61 is used to store the computer program and other programs and data required by the ECG signal measuring device. The memory 61 can also be used to temporarily store data that has been output or is about to be output.

In summary, the embodiment of the present invention provides a control method and control system for filtering a power frequency interference signal, where the control method includes: first rectifying an raw ECG signal of a preset segment for each channel; then obtaining the frequency, amplitude, and phase of the power frequency interference signal in the ECG signal of the rectified preset segment, which are estimated by weighting the signal-to-noise ratio of each channel to obtain the optimal power frequency interference signal of the system; then reconstructing the estimated power frequency interference signal sine wave in combination with the amplitude of each channel; and finally subtracting the reconstructed sine wave from the preset segment of the raw ECG signal to output a clean waveform signal. Thus, the effect is achieved of filtering out the power frequency interference signal without inducing the ringing effect on the signal after a huge transient interference endemic to conventional notch filtering technology, allowing for measurements to be made with high fidelity and accuracy.

It will be apparent to those skilled in the art that, for convenience and brevity of description, only the division of each functional unit and module described above is exemplified. In practical applications, the above functions may be assigned to different functional units as needed. The module is completed by dividing the internal structure of the device into different functional units or modules to perform all or part of the functions described above. Each functional unit and module in the embodiment may be integrated into one processing unit, or each unit may exist physically separately, or two or more units may be integrated into one unit, and the integrated unit may be hardware. Formal implementation can also be implemented in the form of software functional units. In addition, the specific names of the respective functional units and modules are only for the purpose of facilitating mutual differentiation, and are not intended to limit the scope of protection of the present application. For the specific working process of the unit and the module in the foregoing system, reference may be made to the corresponding process in the foregoing method embodiment, and details are not described herein again.

Description.

In the above embodiments, the descriptions of the various embodiments are different, and the parts that are not detailed or described in the specific embodiments may be referred to the related descriptions of other embodiments.

Those skilled in the art will appreciate that the elements and algorithmic steps of the various examples described in connection with the embodiments disclosed herein can be implemented in electronic hardware or a combination of computer software and electronic hardware. Whether these functions are performed in hardware or software depends on the specific application and design constraints of the solution. Those skilled in the art can use different methods for implementing the described functions for each particular application, but such implementation should not be considered to be beyond the scope of the present invention.

In the embodiments provided by the present invention, it should be understood that the disclosed apparatus/terminal device and method may be implemented in other manners. The apparatus/terminal device embodiments described above are merely illustrative. For example, the division of the modules or units is only a logical function division. In actual implementation, there may be another division manner, for example, multiple units. Or components may be combined or integrated into another system, or some features may be omitted or not performed. In addition, the mutual coupling or direct coupling or communication connection shown or discussed may be an indirect coupling or communication connection through some interface, device, or unit, and may be in electrical, mechanical or another form.

The units described as separate components may or may not be physically separated, and the components displayed as units may or may not be physical units, that is, may be located in one place, or may be distributed to multiple network units. Some or all of the units may be selected according to actual needs to achieve the purpose of the solution of the embodiment.

In addition, each functional unit in each embodiment of the present invention may be integrated into one processing unit, or each unit may exist physically separately, or two or more units may be integrated into one unit. The above integrated unit can be implemented in the form of hardware or in the form of a software functional unit.

The integrated modules/units, if implemented in the form of software functional units and sold or used as separate products, may be stored in a computer readable storage medium. Based on such understanding, the present invention implements all or part of the processes in the foregoing embodiments, and may also be completed by a computer program to instruct related hardware. The computer program may be stored in a computer readable storage medium. The steps of the various method embodiments described above may be implemented when the program is executed by the processor. wherein the computer program comprises computer program code, which may be in the form of source code, object code form, executable file, or some intermediate form. The computer readable medium may include any entity or device capable of carrying the computer program code, such as a recording medium, a USB flash drive, a removable hard disk, a magnetic disk, an optical disk, computer memory, read-only memory (ROM), random access memory (RAM, Random Access Memory), electrical carrier signals, telecommunications signals, and software distribution media. It should be noted that the content contained in the computer readable medium may be changed subject to the requirements of legislation and patent practice in a jurisdiction; for example, in some jurisdictions, according to legislation and patent practice, computer readable media does not include electrical carrier signals and telecommunication signals.

The embodiments described above are only for explaining the technical solutions of the present invention, and are not intended to be limiting; although the present invention has been described in detail with reference to the foregoing embodiments, those skilled in the art will understand that the technical solutions described in the examples are modified, or some of the technical features are equivalently replaced, and the modifications or substitutions do not deviate from the spirit and scope of the technical solutions of the embodiments of the present invention, and should be included within the scope of protection of the present invention.

The invention claimed is:

1. A control method for filtering a powerline frequency interference signal, wherein the control method comprises:
   rectifying a raw electrocardiography (ECG) signal in a preset section;
   extracting sinusoidal parameters of the powerline frequency interference signal, said sinusoidal parameters include frequency, amplitude, and phase;
   reconstructing a sine wave according to the said sinusoidal parameters of frequency, amplitude, and phase;
   subtracting a reconstructed powerline frequency interference sinusoidal waveform from the preset section of the raw electrocardiography (ECG) signal to output a clean electrocardiography (ECG) waveform signal;
   wherein an optimal powerline interference frequency extracted from a segment of raw electrocardiography (ECG) signal is determined by the following formula:

$$f_0 = \frac{1}{\sum_{n=1}^{L} \frac{a_n}{SD_n}} \cdot \sum_{n=1}^{L} \frac{a_n}{SD_n} f_n$$

where L is the number of channels with the highest signal-to-noise ratio selected in the raw electrocardiography (ECG) signal, $a_n$ is the amplitude of the powerline frequency interference signal of the nth channel estimated, $SD_n$ is the standard deviation of the nth channel at the current time, $f_n$ is the frequency estimate of the powerline frequency interference signal of the current channel at the current time, and $f_0$ is the optimally estimated frequency of the powerline frequency interference signal of all channels of an entire measurement system;
   wherein the optimal powerline interference amplitude of each ECG channel is determined by the following formula $$A = 2a \frac{\pi \cdot \Delta bin}{\sin(\pi \cdot \Delta bin)} (1 - \Delta bin^2)$$

wherein Δ bin is the bigger difference between the highest discrete frequency bin and the bins prior to and after this highest one.

2. A control method for filtering a powerline frequency interference in accordance with claim 1, wherein before the said rectifying the method further includes:
selecting multi-preset segments in the raw electrocardiography (ECG) signal, wherein each of the preset segments is centered on each QRS (QRS Wave) wavelet, with two adjacent QRS waves serving as reference objects, wherein the end of a first QRS wavelet is defined as the starting point and the beginning of a second QRS wavelet is defined as the ending point.

3. The control method in accordance with claim 1, wherein an optimal phase $\emptyset_0$ of the powerline frequency interference signal obtained in the ECG signal is determined by the following formula: raw electrocardiographv (ECG) signal is determined by the following formula:

$$\emptyset_0 = \frac{1}{\sum_{n=1}^{L} \frac{a_n}{SD_n}} \cdot \sum_{n=1}^{L} \frac{A_n}{SD_n} \emptyset_n$$

where $\emptyset_n$ is the phase of the said powerline interference signal in said nth channel.

4. An ECG signal measuring apparatus comprising a memory, a processor, and a computer program stored in the memory and operable on the processor, wherein the processor, when executing the computer program, implements the steps of the control method according to claim 1.

5. The ECG signal measuring apparatus according to claim 4, wherein before the said rectifying the method further includes:
selecting multi-preset segments in the raw electrocardiography (ECG) signal, wherein each of the preset segments is centered on each QRS (QRS Wave) wavelet, with two adjacent QRS waves serving as reference objects, wherein the end of a first QRS wavelet is defined as the starting point and the beginning of a second QRS wavelet is defined as the ending point.

6. The ECG signal measuring apparatus according to claim claim 4, wherein the optimal phase $\emptyset_0$ of the power frequency interference signal obtained in the said ECG signal is determined by the following formula:

$$\emptyset_0 = \frac{1}{\sum_{n=1}^{L} \frac{a_n}{SD_n}} \cdot \sum_{n=1}^{L} \frac{A_n}{SD_n} \emptyset_n$$

where $\emptyset_n$ is the phase of the said powerline interference in said nth channel.

7. A computer readable storage medium storing a computer program, wherein the computer program is executed by the said processor to implement the said steps of the control method in accordance with claim 1.

8. The computer readable storage medium according to claim 7, wherein before the said rectifying the method further includes:
selecting multi-preset segments in the raw electrocardiography (ECG) signal, wherein each of the preset segments is centered on each QRS (QRS Wave) wavelet, with two adjacent QRS waves serving as reference objects, wherein the end of a first QRS wavelet is defined as the starting point and the beginning of a second QRS wavelet is defined as the ending point.

9. The computer readable storage medium according to claim 7, wherein an optimal phase $\emptyset_0$ of the powerline frequency interference signal obtained in the raw electrocardiography (ECG) signal is determined by the following formula:

$$\emptyset_0 = \frac{1}{\sum_{n=1}^{L} \frac{a_n}{SD_n}} \cdot \sum_{n=1}^{L} \frac{A_n}{SD_n} \emptyset_n$$

where $\emptyset_n$ is the phase of the said powerline frequency interference signal in said nth channel.

10. A control system for filtering power frequency interference signals, wherein the said control system comprises:
a rectifying module, configured to rectify a raw electrocardiography (ECG) signal of a preset segment;
a parameter obtaining module, configured to extract sinusoidal parameters of a powerline frequency interference signal in the raw electrocardiography (ECG) signal of the preset segment, where the sinusoidal parameters include frequency, amplitude, and phase;
a sinewave reconstructing module, configured to reconstruct a sinewave according to the said sinusoidal parameters of frequency, said amplitude, and said phase;
a filtering module, configured to subtract a reconstructed power frequency interference signal sine wave from the preset segment of the raw electrocardiography (ECG) signal and output a clean waveform signal;
wherein an optimal powerline interference frequency extracted from a segment of the raw electrocardiography (ECG) signal is determined by the following formula:

$$f_0 = \frac{1}{\sum_{n=1}^{L} \frac{a_n}{SD_n}} \cdot \sum_{n=1}^{L} \frac{a_n}{SD_n} f_n$$

where L is the number of channels with the highest signal-to-noise ratio selected in the raw electrocardiography (ECG) signal, $a_n$ is the amplitude of the powerline frequency interference signal of the nth channel estimated, $SD_n$ is the standard deviation of the nth channel at the current time, $f_n$ is the frequency estimate of the powerline frequency interference signal of the current channel at the current time, and $f_0$ is the optimally estimated frequency of the powerline frequency interference signal of all channels of an entire measurement system;
wherein the optimal powerline interference amplitude of each ECG channel is determined by the following formula $$A = 2a \frac{\pi \cdot \Delta bin}{\sin(\pi \cdot \Delta bin)} (1 - \Delta bin^2)$$

wherein Δ bin is the bigger difference between the highest discrete frequency bin and the bins prior to and after this highest one.

11. The control system in accordance with claim 10, further includes:

a preset segment dividing module, configured to select multi-preset segments in the raw electrocardiography (ECG) signal, wherein each of the preset segments is centered on each QRS (QRS Wave) wavelet with two adjacent QRS waves serving as reference objects, wherein the end of a first QRS wavelet is defined as the starting point and the beginning of a second QRS wavelet is defined as the ending point.

12. The control system in accordance with claim 10, wherein an optimal phase of the powerline frequency interference signal obtained in the raw electrocardiography (ECG) signal is determined by the following formula:

$$\emptyset_0 = \frac{1}{\sum_{n=1}^{L} \frac{a_n}{SD_n}} \cdot \sum_{n=1}^{L} \frac{A_n}{SD_n} \emptyset_n$$

where $\emptyset_n$ is the phase of the said powerline frequency interference signal in said nth channel.

* * * * *